United States Patent [19]
Ito et al.

[11] Patent Number: 5,454,366
[45] Date of Patent: Oct. 3, 1995

[54] ENDOSCOPE DISTAL END WITH FOLDED CIRCUIT BOARD

[75] Inventors: Keiji Ito; Hiroshi Iwata, both of Tokyo, Japan

[73] Assignee: Asashi Kogaku Kogyo Kabushiki Kaisha, Tokyo, Japan

[21] Appl. No.: 146,462

[22] Filed: Nov. 4, 1993

Related U.S. Application Data

[63] Continuation of Ser. No. 797,973, Nov. 26, 1991, abandoned.

[30] Foreign Application Priority Data

Nov. 27, 1990 [JP] Japan .................... 2-327655

[51] Int. Cl.$^6$ ..................................... A61B 1/04
[52] U.S. Cl. .................. 600/109; 600/128; 600/129
[58] Field of Search ............ 128/4–10; 358/98; 385/117

[56] References Cited

U.S. PATENT DOCUMENTS

| | | | |
|---|---|---|---|
| 4,741,327 | 5/1988 | Yabe | 128/6 |
| 4,832,003 | 5/1989 | Yabe | 128/6 |
| 4,895,138 | 1/1990 | Yabe | 128/6 |
| 4,918,521 | 4/1990 | Yabe et al. | 358/98 |

FOREIGN PATENT DOCUMENTS

| | | | |
|---|---|---|---|
| 62-255913 | 11/1987 | Japan . | |
| 0246714 | 10/1988 | Japan | 128/4 |
| 2156924 | 6/1990 | Japan . | |

*Primary Examiner*—Richard J. Apley
*Assistant Examiner*—John P. Leubecker
*Attorney, Agent, or Firm*—Sughrue, Mion, Zinn, Macpeak & Seas

[57] ABSTRACT

An electronic endoscope having an internal circuit board bearing an electronic circuit arrayed thereon and coupled with a solid-state image pick-up element, with wires of the circuit board connected to lead wires passing through the insertion portion of the endoscope. The circuit board is folded along lines extending the axial direction of the distal end of the insertion portion, so as to divide the circuit board into a plurality of planar surfaces. The electronic circuit wiring portion and the lead wire connecting portion are laid out on the different planar surfaces.

12 Claims, 5 Drawing Sheets

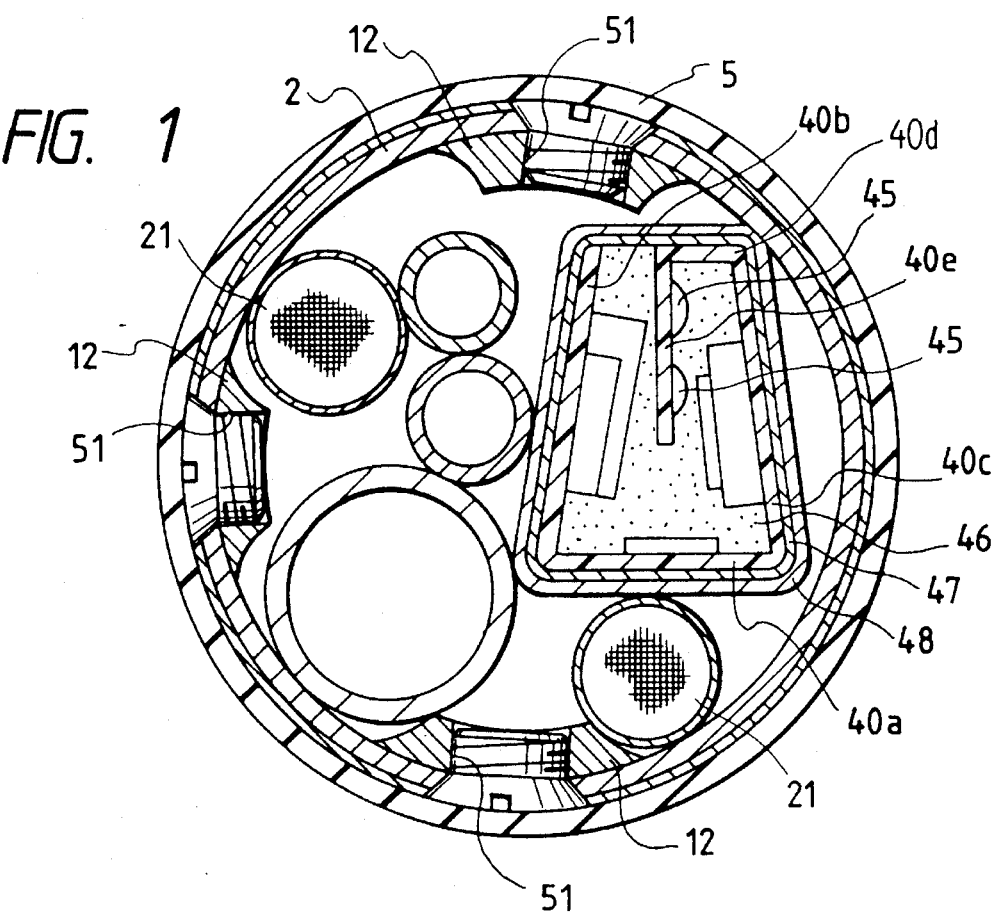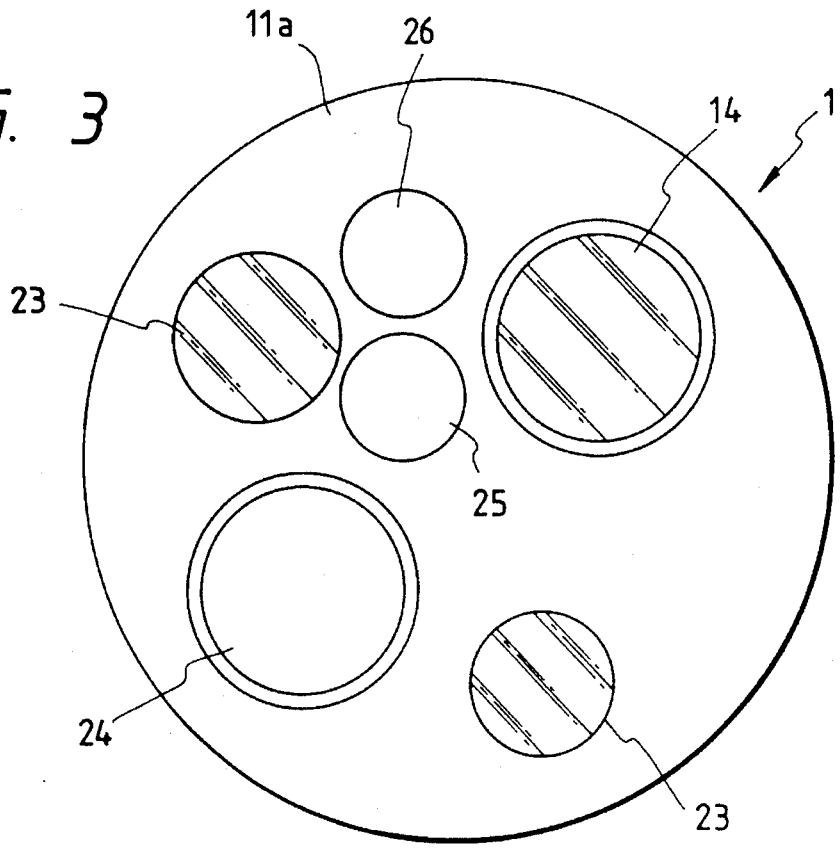

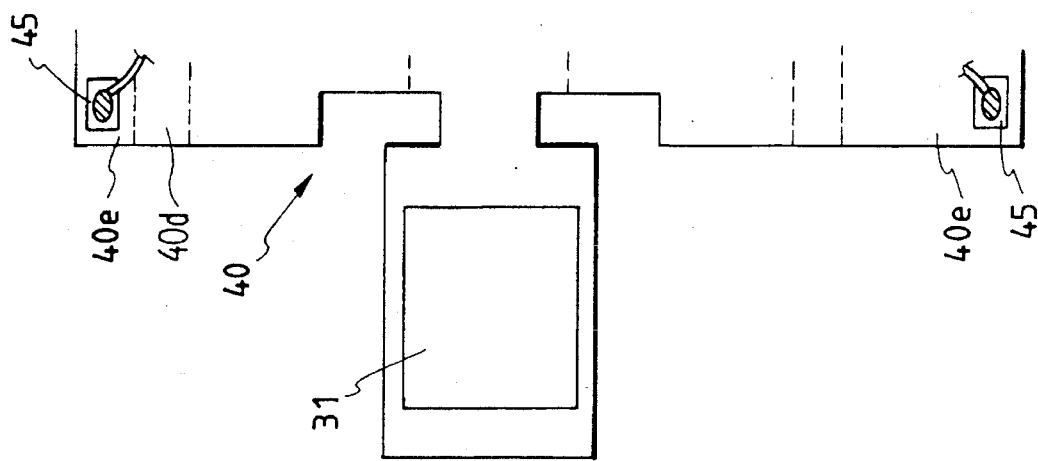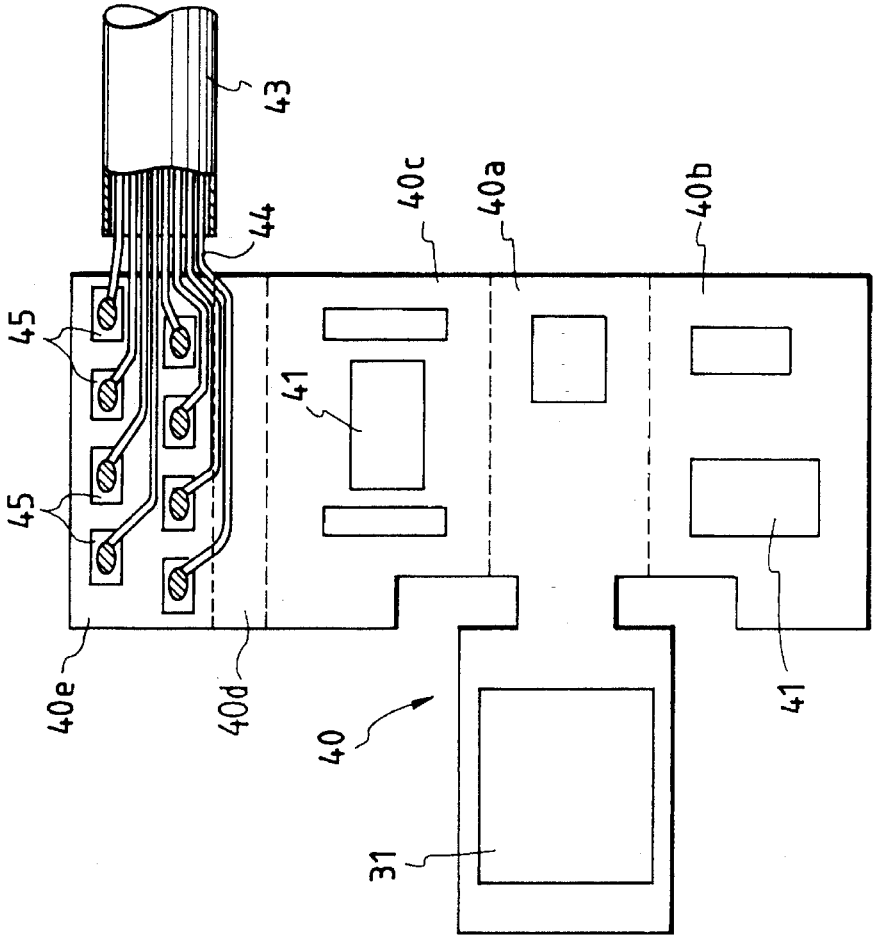

5,454,366

ENDOSCOPE DISTAL END WITH FOLDED CIRCUIT BOARD

This is a Continuation of application Ser. No. 07/797,973 filed Nov. 26, 1991, now abandoned.

BACKGROUND OF THE INVENTION

This application is based on and claims priority from Japanese Application No. HEI 2-327655 filed Nov. 27, 1990, the disclosure of which is incorporated herein.

The present invention relates to a structure of the distal end portion of an electronic endoscope in which a solid-state image pick-up element is contained in the distal end of the insertion portion of the endoscope. In particular, the present invention is a distal end portion of an endoscope having a more compact design than conventional endoscopes.

In a conventional electronic endoscope, a circuit board with electronic circuitry thereon is provided in the vicinity of the solid-state image pick-up element. Lead wires passing through the insertion portion of the endoscope are connected to the electronic circuit so as to provide power, data signals, etc.

FIG. 8 is a perspective view of such a circuit board 101 and associated components. As shown, rectangular prism 103 is disposed at the rear end of objective optical system 102, which extends to the distal side of the insertion portion. An object is imaged on solid-state image pick-up element 104 which is mounted on the circuit board 101, by virtue of reflected light passing through objective optical system 102 and prism 103.

Electronic components 106 are mounted on circuit board 101. The terminals on the rear part of circuit board 101 are soldered to lead wires 107, e.g., as disclosed in Japanese Patent Laid-Open Publication No. Hei. 2-156924.

When lead wires 107 are to be soldered to the rear end portion of circuit board 101, the structure of circuit board 101 must be relatively long so as to provide for terminals. Correspondingly, the rigid part of the distal end of the endoscope is elongated. This makes it difficult to manipulate the endoscope and to insert the same into a body cavity. As a result, some portions of body cavities cannot easily be examined without inflicting pain on a patient.

The electronic circuit wiring portion and the lead wire connecting portion may be arrayed in parallel to each other. However, with such a design, the circuit board dimensions are laterally increased, so that either less space is available for accommodating the surgical instrument channel and other contained members, or the distal end of the endoscope must be designed with a larger diameter. This, of course, also causes limitations as described above.

SUMMARY OF THE INVENTION

The present invention has been made in view of the above circumstances, and it is an object of this invention to provide a structure of the distal end portion of an electronic endoscope which allows the lead wires to be connected to the circuit board without any longitudinal and lateral increase in dimensions of the circuit board and/or the distal end portion.

To achieve the above object, the invention provides a structure of the distal end portion of an electronic endoscope in which a circuit board bearing an electronic circuitry arrayed thereon, and coupled with a solid-state image pick-up element, is provided. Wires of the circuit board are connected to the lead wires passing through the insertion portion of the endoscope. The circuit board is folded along lines extending in the axial direction of the distal end of the insertion portion, so as to divide the circuit board into a plurality of planar surfaces. The electronic circuit wiring portion and the lead wire connecting portion are laid out on different planar surfaces.

With such a structure, the electronic circuit wiring portion and the lead wire connecting portion overlap in the longitudinal direction. Accordingly, the length of the circuit board is not increased. This allows the rigid portion of the endoscope to be short and thus good manipulation and insertion of the endoscope can be obtained.

Further, the circuit board is folded so as to form the planar surface on which the electronic circuit wiring is mounted and the planar surface on which the lead wire connecting portion is mounted. Accordingly, the lateral dimension of the circuit board is not increased. This provides a space within the distal end portion which is large enough to accommodate the contained members therein.

BRIEF DESCRIPTION OF THE DRAWINGS

The invention will be more clearly understood from the following detailed description of the preferred embodiment of the invention with reference to the accompanying drawings, wherein:

FIG. 1 is a cross sectional view taken on line I—I in FIG. 2;

FIG. 3 is a front view showing the endoscope of FIG. 2;

FIG. 5 is a development of a circuit board used in the embodiment of FIG. 2;

FIG. 7 is a development of another circuit board used in the embodiment of FIG. 2.

DETAILED DESCRIPTION OF THE PREFERRED EMBODIMENT

The preferred embodiment of a structure of the distal end portion of an endoscope will now be described in detail with reference to the accompanying drawings.

Figure 2:
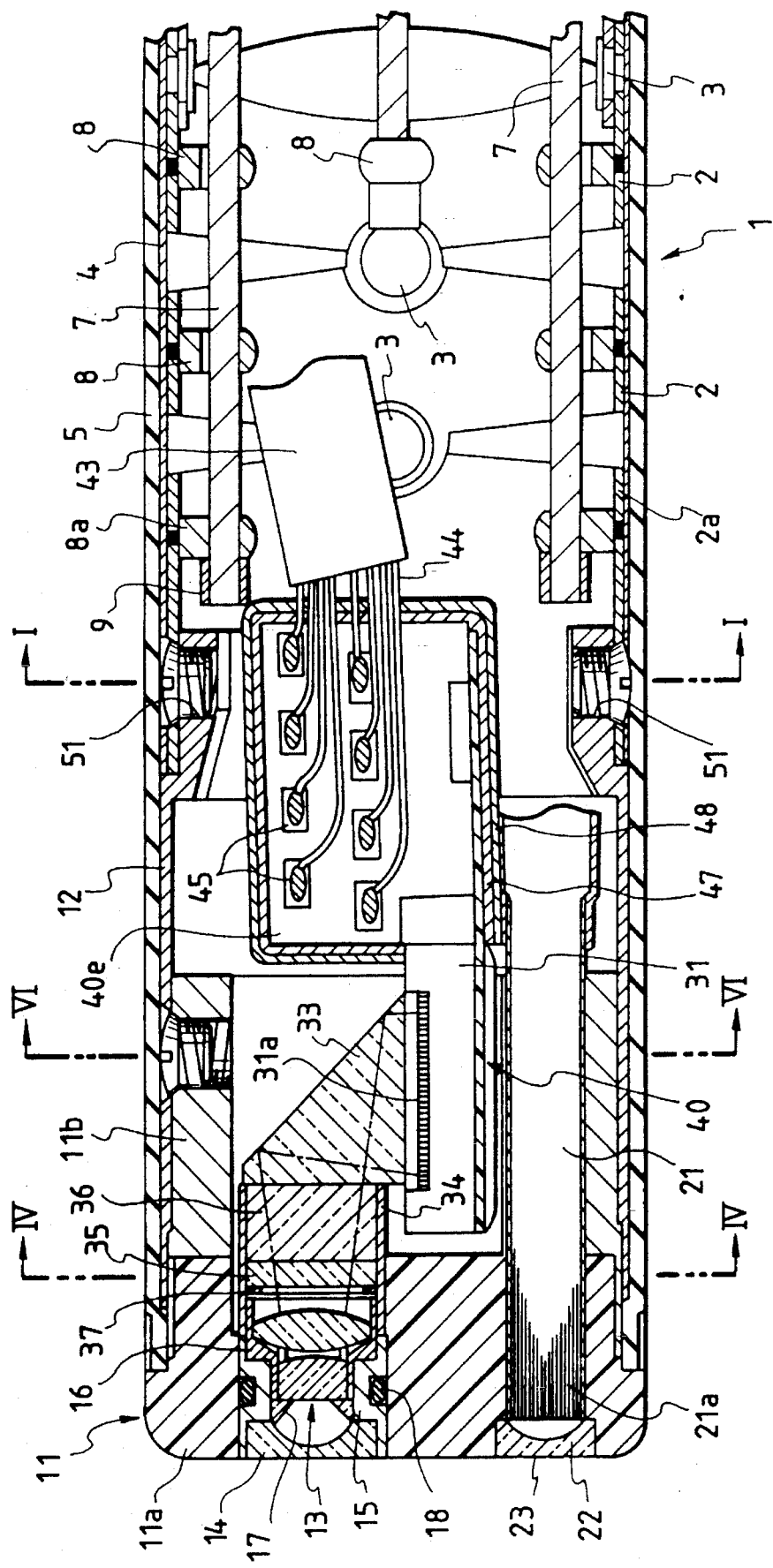
FIG. 2 is a longitudinal sectional view showing the structure of the distal end portion of an endoscope according to an embodiment of the present invention.

FIG. 2 is a longitudinal sectional view showing a structure of the distal end portion of an endoscope according to an embodiment of the present invention. Bendable portion 1 of the distal end of a slender, flexible pipe, serves as an insertion portion of the endoscope. In bendable portion 1, a plurality of nodal rings 2 are rotatably coupled with each other by means of rivets 3. Nodal rings 2 are covered with mesh tube 4, made of fine metal wires and sheathing 5 made of rubber, or the like.

Bendable operating wires 7, which can be remotely manipulated, are retractably placed within wire guide 8 which protrudes inwardly from nodal rings 2 respectively. The tip of bendable operating wires 7 are fixed to wire guide 8, which is provided in the nodal ring 2a closest to the distal end of the insertion portions, by silver brazing, or the like. Stopper pipe 9 is fixed to the end of wire guide 8a, by silver brazing so as to prevent operating wire 7 from slipping off of the wire guide 8.

Distal end body 11 is coupled with the tip of bendable portion 1 by means of coupling tube 12. Distal end body 11 is formed with metal body part 11b and head part 11a made of electrically insulating plastic, which is coupled with the distal side of metal body part 11b. Distal end body 11 is circular in cross section when seen from the distal end (the left side in FIG. 2). Objective optical system 13 is contained within head part 11a.

Objective optical system 13 consists of a plurality of lenses, and is axially coincident with distal end body 11. Light from an observed object is made incident to the incident side surface of the objective optical system (the left side in FIG. 2). View window 14 consists of the foremost lens of objective optical system 13. Lens barrels 15 and 16 hold respective lenses of objective optical system 13. Lens barrel 15 is bonded to head part 11a of distal end body 11. Aperture diaphragm 17 is provided in behind of the view window 14, and O-ring 18 is provided for sealing purposes between head part 11a and lens barrel 15.

Light emitting end 21a of light guide fiber bundle 21 is secured to head part 11a so as to be axially in parallel with objective optical system 13. Concave lens 22, for distributing light, is disposed on the distal end face of light emitting end 21a. Thus, concave lens 22 forms illumination window 23. Light transmitted through light guide fiber bundle illuminates an object located ahead of distal end body 11.

FIG. 3 is a front view showing head part 11a of distal end body 11. Two illumination windows 23 are provided, and an associated light guide fiber bundle 21 is disposed on the inner side of each window 23. Port 24 is provided through which surgical instruments, such as forceps, can be inserted. Port 24 may be provided for suction. Air-feed nozzle 25 and water-feed nozzle 26 are also provided to clean the surface of the view window, respectively on head part 11a.

Returning to FIG. 2, solid-state image pick-up element 31 is disposed within body part 11b. Solid-state image pick-up element 31 may be a CCD (charge coupled diode), or the like. Light receiving surface 31a of solid-state image pick-up element 31 is rectangular or square, and is disposed in parallel with the optical axis of objective optical system 13.

Prism 33 is disposed between objective optical system 13 and solid-state image pick-up element 31, and is positioned such that the optical axis of the objective optical system 13 is perpendicular to the center axis of the light-receiving surface 31a of the solid-state image pick-up element 31. Light passing through objective optical system 13 will then be reflected toward the light receiving surface 31a.

Within optical coupling tube 34, coupled with the later half of lens barrel 16, flare mask 37, color correction filter 35, and low-pass filter 36 are disposed between prism 33 and objective optical system 13. With such a structure, light reflected from an object (not shown) located on the left side in FIG. 2 falls incident on the light receiving surface 31a of the solid-state image pick-up element 31, through objective optical system 13 and prism 33.

Figure 4:
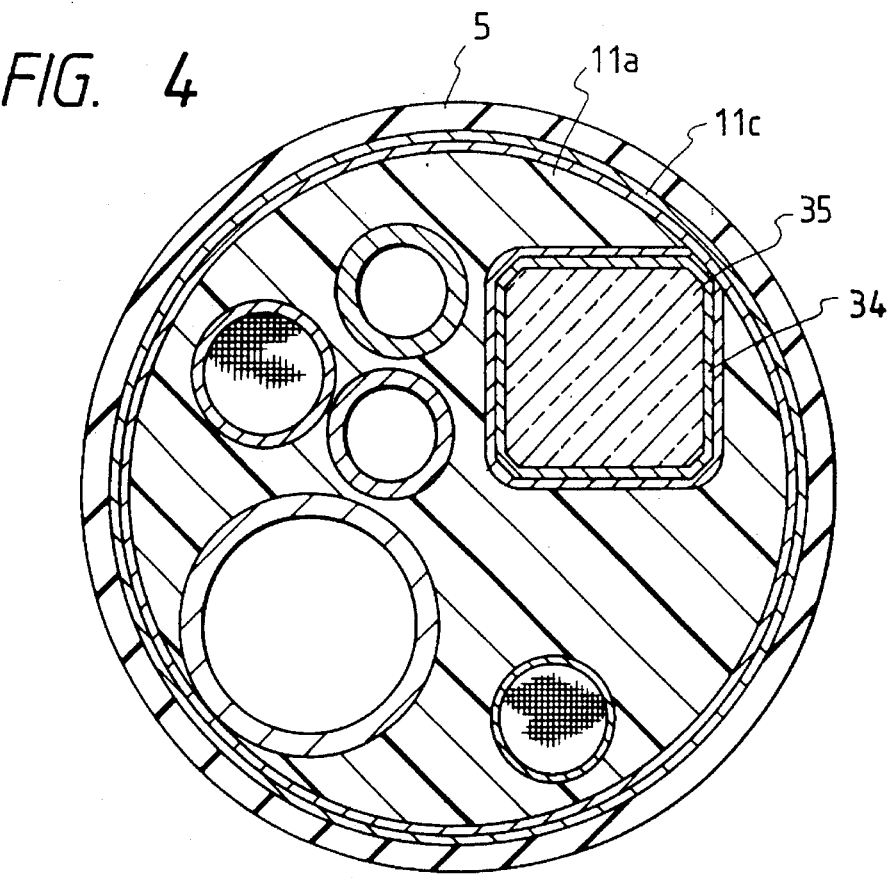
FIG. 4 is a cross sectional view taken on line IV—IV in FIG. 2.

As shown in FIG. 4, optical coupling tube 34 and the optical elements disposed therewithin are shaped to be substantially square in cross section, with the four corners, which are unnecessary to transmit the light beam, cut-off. In this embodiment, objective optical system 13 is designed such that the principal ray traveling from the observed object through the objective to solid-state image pick-up element 31 gradually diverge as indicated by one-dot-chain lines in FIG. 2. Solid-state image pick-up element 31, unlike a conventional light guide fiber bundle, is capable of receiving light with low loss even if light is relatively obliquely incident thereon. It is for this reason that objective optical system 13 can be of a type in which a principal ray diverges.

Figure 6:
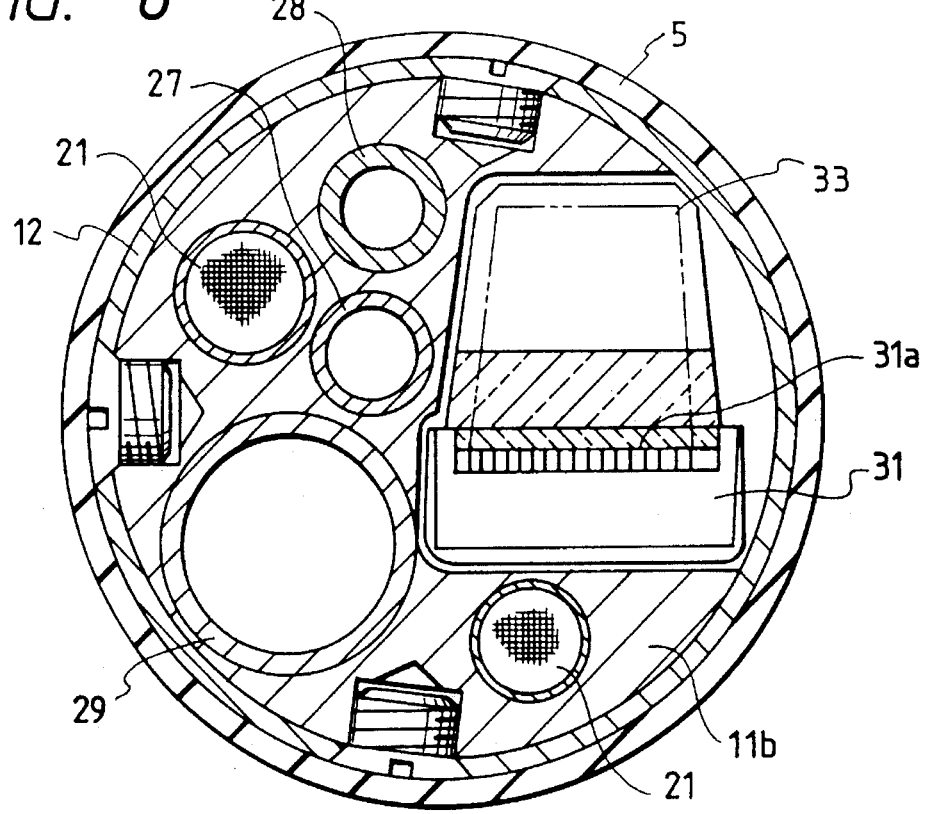
FIG. 6 is a cross sectional view taken on line VI—VI in FIG. 2.
Figure 8:
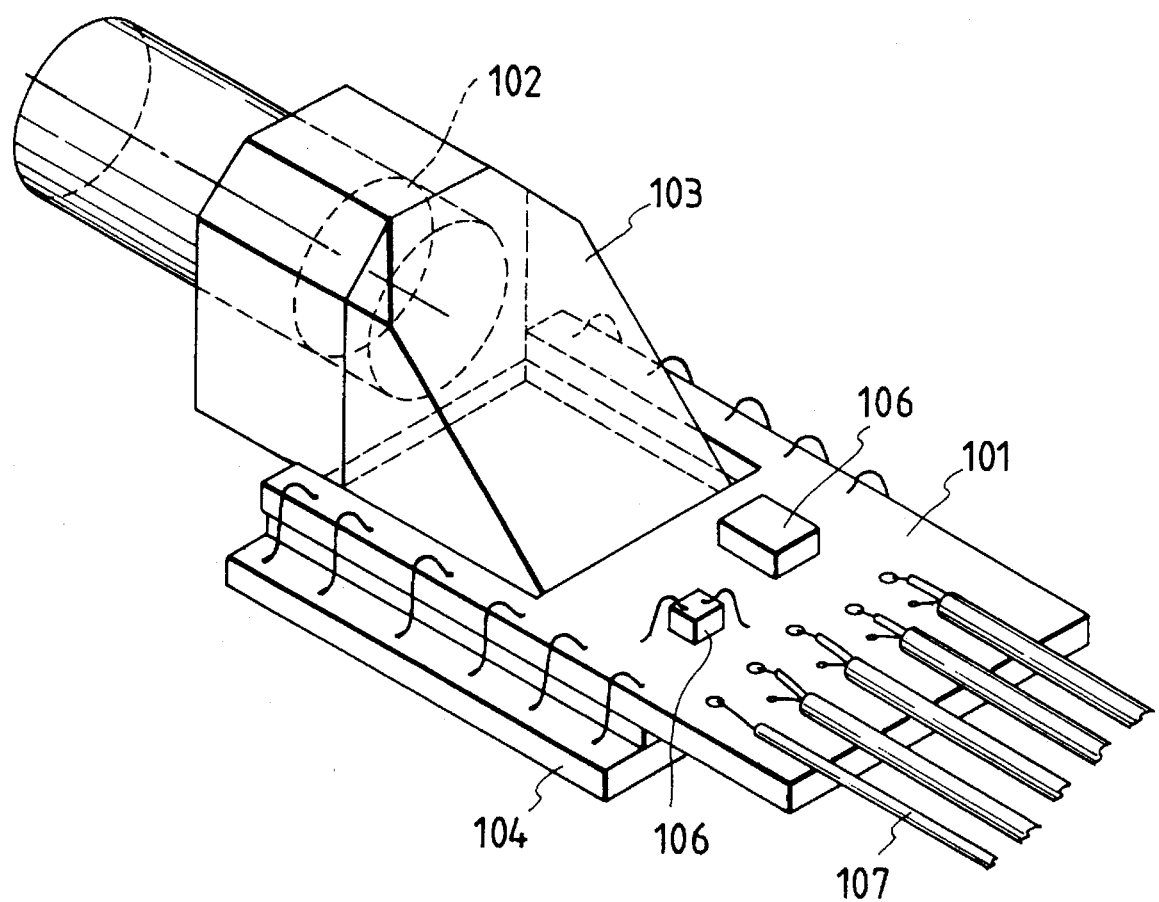
FIG. 8 is a perspective view showing a conventional structure of the distal end portion of an endoscope.

The outer configuration of rays of light passing through prism 33 also gradually diverge toward light receiving surface 31a, as indicated by a two-dot-chain line in FIG. 6. Prism 33 is thus shaped like a trapezoid of which nonparallel sides gradually diverge toward light receiving surface 31a, i.e., it is substantially parallel to the outer configuration of the rays of light passing therethrough. This shape of prism 33 minimizes the area occupied by prism 33 in distal end body 11. Accordingly, it allows distal end body 11 to be small in cross section.

Air-feed pipe 27 and water-feed pipe 28 are provided in the endoscope, which are connected to nozzles 25, 26, respectively as illustrated in FIG. 6. Surgical instrument insertion pipe 29 is also provided to allow forceps, or the like, to pass through the endoscope.

Circuit board 40, to which solid-state image pick-up element 31 is mounted, consists of a flexible, electrically insulating plastic plate, as shown in FIG. 7. Circuit board 40 is divided into five planar surfaces 40a–40e which are separated by folding lines which extend in the axial direction of distal end body 11, and which are indicated by broken lines in FIG. 5, so that circuit board 40 may be folded along these lines.

Electronic circuits coupled with solid-state image pick-up element 31 are formed on planar surfaces 40b and 40c, which are on both sides of planar surface 40a. Various electronic parts are mounted on planar surfaces 40b and 40c. Terminals 45 are formed on the uppermost planar surface 40e of circuit board 40. Lead wires 44 of cable 43, which are inserted into bendable portion 1 from the flexible tube of the endoscope, are soldered to terminals 45.

Circuit board 40, defines a space which is four-sided (i.e., tetragonal) in cross-section. In other words, it is shaped like a trapezoid after folding, as viewed from objective optical system 13, and is similar in shape to the outer configuration of prism 33, as shown in FIG. 1. Circuit board 40 is located on the rear side of prism 33. The outer edge of prism 33 closely overlaps with circuit board 40 when viewed from objective optical system 13.

Planar surface 40e, with terminals 45, is bent downward at the center of the upper shorter side of the trapezoid defined by circuit board 40. The space within the trapezoid defined by circuit board 40 is filled with electrically insulating plastic. Accordingly, terminals 45 extend neither rearwardly nor sideways, leading to reduction in the length and the width of circuit board 40. If two cables 43 are used, it is advisable to use a circuit board 40 having two planar surfaces 40e with terminals 45 and folded so as to extend inward on both ends thereof as shown in FIG. 7, to which lead wires are soldered respectively.

An outer peripheral surface of circuit board 40, after being folded and shaped like a trapezoid, is covered by electrical conducting body 47 along the surface of circuit board 40 so as to form an electrical shielding layer.

Electrical conducting body 47 is also shaped like a trapezoid as viewed from objective optical system 13. Further, an outer surface of electrical conducting body 47 is covered by electrical insulating member 48 in such a manner that an electrical current leakage is prevented from occurring.

Returning to FIG. 2, coupling tube 12 surrounding the circuit board 40 is tubular in shape, except at a rear part thereof (right side in FIG. 2). The distal part of coupling tube 12 is fitted around body part 11b of distal end body 11.

The rear part of coupling tube 12 is fixed to the foremost nodal ring 2a by means of screws. To provide adequate strength around holes 51 for receiving screws, the inner diameter of the rear end portion of the coupling tube 12 in the proximity of screw holes 51 is smaller than that of remaining portions thereof. That is, the thickness of the rear end, proximate screw holes 51, is larger than that of remaining portions.

This can be accomplished by machining out the rear end portion of coupling tube 12, at portions other than the three portions proximate screw holes 51 formed, as shown in FIG. 1. Within the portion ranging from bendable portion 1 to coupling tube 12, the available space extends all the way to the inner circumferential surfaces of the nodal rings 2, except the space proximate screw-holes 51. As a result, a space large enough to accommodate the respective members to be contained therein is ensured.

In the above-mentioned embodiment of the invention, the rear end portion of coupling tube 12, other than three portions in the proximity of screw holes 51 formed therein, are machined so as to be cut off. However, it is also possible to employ a coupling tube having a rear end portion in which only portions interfering with accommodated respective members to be contained in coupling tube are machined out so as to be cut off.

Coupling tube 12 may be coupled with the foremost nodal ring 2 by means of any suitable coupling means such as silver brazing, spot welding, or the like. Sheathing tube 5 covers the rear part of distal the end body 11.

As seen from the foregoing description, according to the present invention, the electronic circuit wiring portion and the lead wire connecting portion are not arrayed longitudinally. Accordingly, the longitudinal size of the circuit board is not increased. This allows a rigid part of the distal end portion of the endoscope to be small in length, thus allowing good manipulation and insertion of the endoscope.

Additionally, the circuit board is folded to form the planar surfaces of the circuit board on which the electronic circuit wiring portion is mounted and another planar surface on which the lead wire connecting portion is mounted. Accordingly, the lateral dimension of the circuit board is not increased. This design ensures a space within the distal end portion which is large enough to accommodate the contained members therein.

While there has been described what is at the present considered to be the preferred embodiment of the invention, it will be understood by those skilled in the art that various changes may be made to the disclosed embodiment without departing from the spirit and scope of the invention as defined in the appended claims.

What is claimed is:

1. An electronic endoscope having an insertion portion with a distal end having a longitudinal axis, said distal end containing an electronic circuit board having an electronic circuit portion supporting electronic circuit components and a wiring portion for connection of lead wires which pass through said insertion portion back toward an operator end of said endoscope, wherein said circuit board is folded along lines extending substantially parallel to said longitudinal axis so as to divide said circuit board into a plurality of planar surfaces, at least four of which collectively define a tetragonal space and are provided with said electronic circuit portion thereon, and at least one of which extends into an interior of said tetragonal space and is provided with said wiring portion thereon.

2. An endoscope according to claim 1, wherein said tetragonal space is a trapezoidal space, said at least one of said planar surfaces extending into said space from one side of said trapezoidal space.

3. An endoscope as claimed in claim 2, wherein said one side comprises an upper short side of said trapezoidal space.

4. An endoscope as claimed in claim 2, wherein said space is filled with electrically insulating material.

5. An endoscope as claimed in claim 4, wherein said circuit board is a plate made of electrically insulating material.

6. An endoscope according to claim 2, wherein electronic parts are mounted on a side of the at least four planar surfaces within said space.

7. An endoscope as claimed in claim 2, said at least one of said planar surfaces extending from a central portion of said one side of said trapezoidal space.

8. An endoscope as claimed in claim 1, further comprising a solid-state image pick-up element within said distal end portion and coupled to said electronic circuit.

9. An electronic endoscope having an insertion portion, a distal end of said insertion portion containing a circuit board, said circuit board comprising:

a planar rectangular base portion;

two planar rectangular side portions, said side portions being connected at lower edges thereof to side edges of said base portion, said side portions extending from said base portion at substantially equal angles with respect to said base portion, upper edges of said side portions defining a gap therebetween;

a planar rectangular top portion extending from one of said upper edges across substantially one half of said gap, said top portion being parallel with said base portion; and a planar rectangular terminal portion having connection terminals disposed thereon, said terminal portion extending from a remote free edge of said top portion toward said base portion; electronic components being disposed only on at least one of said planar rectangular base portion, said two planar rectangular side portions and said planar rectangular top portion.

10. An electronic endoscope as claimed in claim 9, further comprising:

a second top portion which is planar and rectangular, said second top portion extending from the other of said upper edges, in cantilever fashion, across substantially one half of said gap; and a second terminal portion which is planar and rectangular, said second terminal portion having connection terminals disposed thereon, said second terminal portion extending from a remote free edge of said second top portion toward said base portion.

11. An electronic endoscope as claimed in claim 9, wherein said terminal portion extends at a right angle with respect to said top portion.

12. An electronic endoscope having an insertion portion with a distal end having a longitudinal axis, said distal end containing an optical prism and an electronic circuit board, said electronic circuit board having an electronic circuit portion supporting electronic circuit components and a wiring portion for connection of lead wires which pass through said insertion portion back toward an operator end of said endoscope, wherein said circuit board is folded along lines extending substantially parallel to said longitudinal axis so as to divide said circuit board into a plurality of planar surfaces which define a tetragonal space, at least one of said planar surfaces extending into an interior of said tetragonal space and being provided with said wiring portion thereon, said at least one of said planar surfaces being entirely contained within an area defined by a cross-section of said prism as viewed along said longitudinal axis.

* * * * *

UNITED STATES PATENT AND TRADEMARK OFFICE
CERTIFICATE OF CORRECTION

PATENT NO. : 5,454,366

DATED : October 3, 1995

INVENTOR(S) : Ito et al.

It is certified that error appears in the above-indentified patent and that said Letters Patent is hereby corrected as shown below:

On the cover sheet, Section [73], please correct the Assignee to read:

--Asahi Kogaku Kogyo Kabushiki Kaisha, Tokyo, Japan--

Signed and Sealed this

Fifth Day of August, 1997

Attest:

BRUCE LEHMAN

Attesting Officer

Commissioner of Patents and Trademarks